(12) United States Patent
Salamone et al.

(10) Patent No.: US 8,053,205 B2
(45) Date of Patent: *Nov. 8, 2011

(54) DOXORUBICIN IMMUNOASSAY

(75) Inventors: Salvatore J. Salamone, Stockton, NJ (US); Jodi Blake Courtney, Doylestown, PA (US); Shu He, Allentown, PA (US)

(73) Assignee: Saladax Biomedical Inc., Bethlehem, PA (US)

( * ) Notice: Subject to any disclaimer, the term of this patent is extended or adjusted under 35 U.S.C. 154(b) by 189 days.

This patent is subject to a terminal disclaimer.

(21) Appl. No.: 12/433,111

(22) Filed: Apr. 30, 2009

(65) Prior Publication Data

US 2009/0215082 A1   Aug. 27, 2009

Related U.S. Application Data

(62) Division of application No. 11/389,934, filed on Mar. 27, 2006, now Pat. No. 7,569,358.

(60) Provisional application No. 60/666,288, filed on Mar. 30, 2005.

(51) Int. Cl.
*G01N 33/53* (2006.01)
*G01N 33/543* (2006.01)
*C07K 1/10* (2006.01)
*C07K 1/04* (2006.01)

(52) U.S. Cl. ........ 435/7.93; 435/7.1; 436/518; 436/523; 530/402; 530/403; 530/389.9; 530/807

(58) Field of Classification Search .................. None
See application file for complete search history.

(56) References Cited

U.S. PATENT DOCUMENTS

| | | | |
|---|---|---|---|
| 5,122,368 | A | 6/1992 | Greenfield et al. |
| 5,177,016 | A | 1/1993 | Balsari et al. |
| 5,824,805 | A | 10/1998 | King et al. |
| 6,146,658 | A | 11/2000 | Bosslet et al. |
| 2002/0119095 | A1 | 8/2002 | Gabathuler |

FOREIGN PATENT DOCUMENTS

| | | |
|---|---|---|
| EP | 0316776 | 5/1989 |
| WO | 0213843 | 2/2002 |

OTHER PUBLICATIONS

Chen et al., "Synthesis of Doxorubicin Conjugates Through Hydrazone Bonds to Melanotransferrin P97," Synthetic Communications, vol. 33, Issue 14 Jan. 2003, pp. 2377-2390.
King et al., "Monoclonal Antibody Conjugates of Doxorubicin Prepared with Branched Linkers: A Novel Method for Increasing the Potency of Doxorubicin Immunoconjugates," Bioconjugate Chem., 1999, 10 (2), pp. 279-288.
King et al., "Monoclonal Antibody Conjugates of Doxorubicin Prepared with Branched Peptide Linkers: Inhibition of Aggregation by Methoxytriethyleneglycol Chains," J. Med. Chem., 2002, 45 (19), pp. 4336-4343.
Kratz et al., "Probing the cysteine-34 position of endogenous serum albumin with thiol-binding doxorubicin derivatives. Improved efficacy of an acid-sensitive doxorubicin derivative with specific albumin-binding properties compared to that of the parent compound," J Med Chem. Dec. 5, 2002;45(25):5523-33.
Kratz et al., "Preparation, characterization and in vitro efficacy of albumin conjugates of doxorubicin," Biol Pharm Bull. Jan. 1998;21(1):56-61.
Lau et al., "Novel doxorubicin-monoclonal anti-carcinoembryonic antigen antibody immunoconjugate activity in vitro," Bioorganic & Medicinal Chemistry vol. 3, Issue 10, Oct. 1995, pp. 1305-1312.
Scott et al., "Synthesis of reagents for the one step incorporation of hydrazide functionality onto the lysine residues of proteins, and their use as linkers for carbonyl containing molecules,"Bioorganic & Medicinal Chemistry Letters vol. 6, Issue 13, Jul. 9, 1996, pp. 1491-1496.
Watanabe et al., "Measurement of Cross-Reactive Properties of Adriamycin Derivatives by the Inhibition Enzyme-Linked Immunosorbent Assay for Adriamycin," Tokai journal of experimental and clinical medicine 15(4), pp. 327-334, Jul. 1990.
Zhou et al., "Cell-specific delivery of a chemotherapeutic to lung cancer cells," J Am Chem Soc. Dec. 8, 2004;126 (48):15656-7.
The partial European Search Report by the European Patent Office, issued on Oct. 19, 2010, in the European application No. 10007967.2.
The extended European Search Report by the European Patent Office, issued on Jan. 21, 2009, in the European application No. 06739675.4.

*Primary Examiner* — Shafiqul Haq

(57) ABSTRACT

Novel conjugates of doxorubicin and novel doxorubicin immunogens derived from the 13 and 14 positions of doxorubicin and antibodies generated by these doxorubicin linked immunogens all of which are useful in immunoassays for the quantification and monitoring of doxorubicin in biological fluids.

11 Claims, No Drawings

DOXORUBICIN IMMUNOASSAY

CROSS-REFERENCE TO RELATED APPLICATION

This Application is a Divisional of application Ser. No. 11/389,934 filed Mar. 27, 2006, now U.S. Pat. No. 7,569,358 which claims the benefit of Provisional Application Ser. No. 60/666,288, filed Mar. 30, 2005. Each of prior mentioned applications is hereby incorporated by reference.

FIELD OF THE INVENTION

This invention relates to the field of immunological assays for determining the presence and/or quantifying the amount of doxorubicin and pharmaceutically active metabolites in human biological fluids in order to rapidly determine optimal drug concentrations during chemotherapy.

BACKGROUND OF THE INVENTION

Cancer is a term used to describe a group of malignancies that all share the common trait of developing when cells in a part of the body begin to grow out of control. Most cancers form as tumors, but can also manifest in the blood and circulate through other tissues where they grow. Cancer malignancies are most commonly treated with a combination of surgery, chemotherapy, and/or radiation therapy. The type of treatment used to treat a specific cancer depends upon several factors including the type of cancer malignancy and the stage during which it was diagnosed.

Doxorubicin, also known as Adriamycin, is one of the more common cytotoxic agents used for the treatment of breast cancer. Adriamycin which is the commercial hydrochloride salt of doxorubicin has the formula:

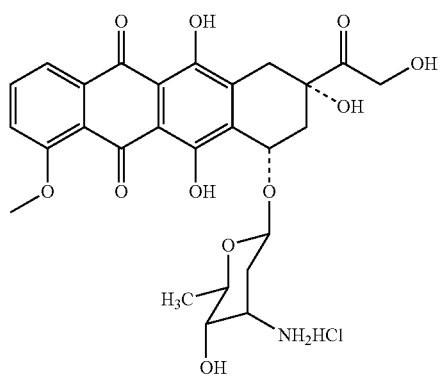

I

This compound has been associated with debilitating side effects such as cardiotoxicity, myelosuppression, hypersensitivity, nausea and vomiting. By monitoring the levels of doxorubicin in the body and adjusting the dose these side effects can be better controlled and limited in patients.

At the same time, there is often highly variable relationship between the dose of doxorubicin and the resulting serum drug concentration that affects therapeutic effect. The degree of intra- and inter-individual pharmacokinetic variability of doxorubicin can be as high as 5-fold and is impacted by many factors, including:
Organ function
Genetic regulation
Disease state
Age
Drug-drug interaction
Time of drug ingestion,
Mode of drug administration, and
Technique-related administration.

As a result of this variability, equal doses of the same drug in different individuals can result in dramatically different clinical outcomes (Hon et. al. *Clinical Chemistry* 44, pp 388-400, 1998). The effectiveness of the same doxorubicin dosage varies significantly based upon individual drug clearance and the ultimate serum drug concentration in the patient. Therapeutic drug management would provide the clinician with insight on patient variation in intravenous drug administration. With therapeutic drug management, drug dosages could be individualized to the patient, and the chances of effectively treating the cancer, without the unwanted side effects, would be much higher.

In addition, therapeutic drug management of doxorubicin would serve as an excellent tool to ensure compliance in administering chemotherapy with the actual prescribed dosage and achievement of the effective serum concentration levels. It has been found that variability in serum concentration is not only due to physiological factors, but can also result from variation in administration technique.

Routine therapeutic drug management of doxorubicin would require the availability of simple automated tests adaptable to general laboratory equipment. Tests that best fit these criteria are immunoassays such as a radioimmunoassay and an enzyme-linked immunosorbent assay. However the corresponding antibodies used in these immunoassays must demonstrate a broad cross-reactivity to doxorubicin, without any substantial activity to non-pharmaceutically active doxorubicin metabolites. In order to be effective in monitoring drug levels of doxorubicin, the antibody should be most specific to the active compound, doxorubicin and display very low cross-reactivity to no cross-reactivity to the non-pharmaceutically active metabolites of doxorubicin particularly doxorubicin aglycone which has the formula:

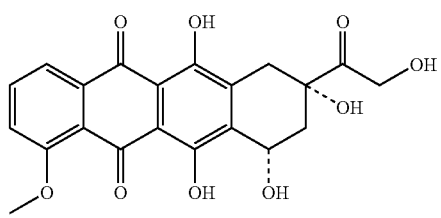

I-A

SUMMARY OF INVENTION

In accordance with this invention, a new class of antibodies have been produced which are substantially selectively reactive to doxorubicin so as to bind to doxorubicin without any substantial cross reactivity to non-pharmaceutically active doxorubicin metabolites, particularly doxorubicin aglycone. By selectively reactive, it is meant that this antibody only reacts with the pharmaceutically active doxorubicin molecule and does not substantially react with the non-pharmaceutically active doxorubicin metabolites, the most important blocking metabolites being doxorubicin aglycone.

It has been found that by using immunogens which are conjugates of an immunogenic carrier having a reactive thiol or amino functional group with 13 substituted doxorubicin compounds of the formula:

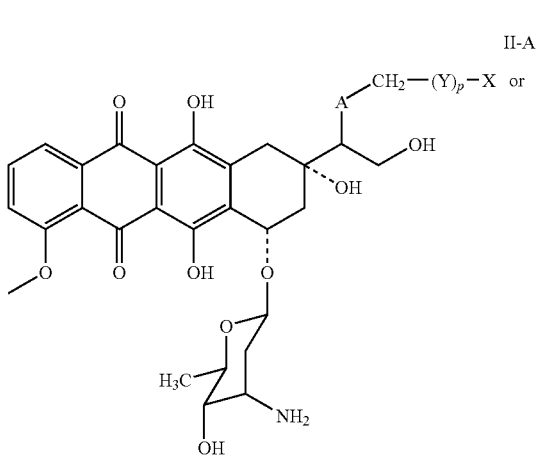

wherein A is

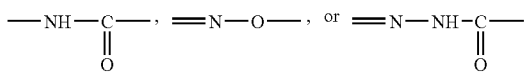

Y is an organic spacing group;

X is a functional group capable of binding to said carrier through said amino or thiol group; and p is an integer from 0 to 1 or compounds of the formula:

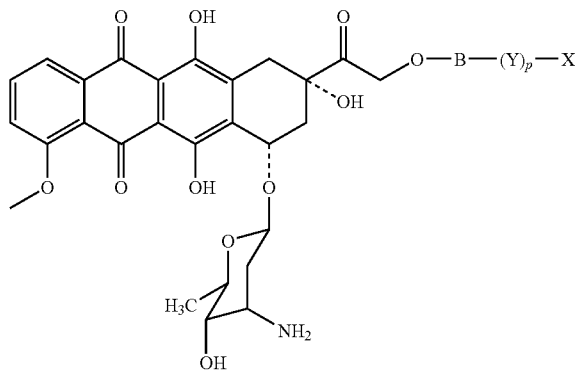

wherein p, Y and X are as above and B is —$CH_2$— or

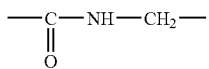

or mixtures thereof; produce antibodies which are specific for doxorubicin and do not substantially react with or bind with non-pharmaceutical active metabolites particularly doxorubicin aglycone. The provision of these antibodies which substantially selectively react with doxorubicin and do not cross react with pharmaceutically inactive metabolites particularly doxorubicin aglycone allows one to produce an immunoassay which can specifically detect and monitor doxorubicin in the fluid samples of patients being treated with doxorubicin. Also included within this invention are reagents and kits for said immunoassay.

DETAILED DESCRIPTION

In accordance with this invention, a new class of antibodies is provided which substantially selectively react with doxorubicin and do not substantially react or cross react with pharmaceutically inactive doxorubicin metabolites mentioned hereinabove. It has been discovered that through the use of these derivatives of 13-oxo substituted doxorubicin of formula II-A and/or of the 14-hydroxy substituted doxorubicin of formula II-B or mixtures thereof, as immunogens, this new class of antibodies of this invention are provided. It is through the use of these antibodies that an immunoassay, including reagents and kits for such immunoassay for detecting and/or quantifying doxorubicin in blood, plasma or other body fluid samples has been developed. By use of this immunoassay, the presence and amount of doxorubicin in body fluid samples, preferably a blood or plasma sample, can be detected and/or quantified. In this manner, a patient being treated with doxorubicin can be monitored during therapy and his treatment adjusted in accordance with said monitoring. By means of this invention one achieves the therapeutic drug management of doxorubicin in cancer patients being treated with doxorubicin as a chemotherapeutic agent.

The reagents utilized in the assay of this invention are conjugates of a carrier containing a reactive thiol or amino group with the compounds of formula II-A and II-B or mixtures thereof. Preferably the carriers contain a polyamine polymer, which contains a reactive thiol or amino group. In the immunogens the carriers preferably contain a polyamine polymer, which contains a reactive thiol or amino group. These conjugates are competitive binding partners with the doxorubicin present in the sample for the binding with the antibodies of this invention. Therefore, the amount of conjugate reagent which binds to the antibody will be inversely proportional to the amount of doxorubicin in the sample. In accordance with this invention, the assay utilizes any conventional measuring means for detecting and measuring the amount of said conjugate which is bound or unbound to the antibody. Through the use of said means, the amount of the bound or unbound conjugate can be determined. Generally, the amount of doxorubicin in a sample is determined by correlating the measured amount of the bound or unbound conjugate produced by the doxorubicin in the sample with values of the bound or unbound conjugate determined from a standard or calibration curve obtained from samples containing known amounts of doxorubicin, which known amounts are in the range expected for the sample to be tested. These studies for producing calibration curves are determined using the same immunoassay procedure as used for the sample.

The conjugates which include the immunogens, are prepared from compounds of the formula II-A or II-B or mixtures thereof. The carriers including the immunogens having a reactive terminal amino or thiol group are linked to the ligand portions which have the formula:

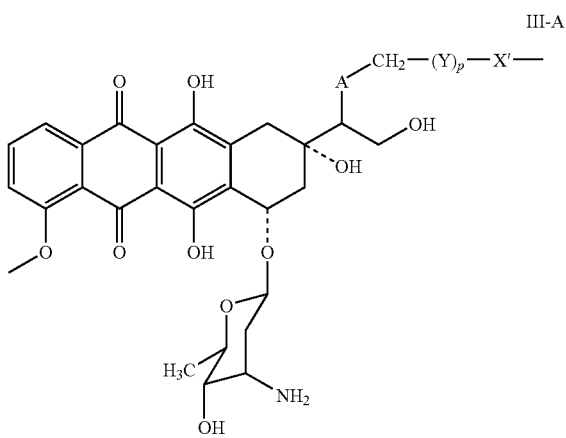

III-A wherein Y, A and p are as above; and
X' is —CH$_2$— or a functional linking group;
compounds of the formula:

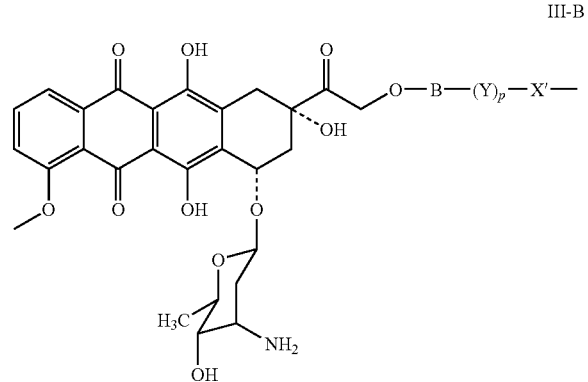

III-B wherein X', Y, B and p are as above.

These ligand portions may be linked to one or more active thiol or amino sites on the carrier containing the polyamine polymer. Preferably these carriers contain a polymer, most preferred a polyamine polymer, containing a reactive thiol or amino group.

DEFINITIONS

Throughout this description the following definitions are to be understood:

The term doxorubicin includes doxorubicin as well as the pharmaceutically acceptable salts of doxorubicin.

The terms "immunogen" and "immunogenic" refer to substances capable of eliciting, producing, or generating an immune response in an organism.

The term "conjugate" refers to any substance formed from the joining together of two parts. Representative conjugates in accordance with the present invention include those formed by the joining together of a small molecule, such as the compound of formula II-A and II-B, and a large molecule, such as a carrier or a polyamine polymer, particularly protein. In the conjugate the small molecule may be joined at one or more active sites on the large molecule. The term conjugate includes the term immunogen.

"Haptens" are partial or incomplete antigens. They are carrier-free substances, mostly low molecular weight substances, which are not capable of stimulating antibody formation, but which do react with antibodies. The latter are formed by coupling a hapten to a high molecular weight immunogenic carrier and then injecting this coupled product, i.e., immunogen, into a human or animal subject. The hapten of this invention is doxorubicin.

As used herein, a "spacing group" or "spacer" refers to a portion of a chemical structure which connects two or more substructures such as haptens, carriers, immunogens, labels, or tracers through a CH$_2$ or functional linking group. These spacer groups will be enumerated hereinafter in this application. The atoms of a spacing group and the atoms of a chain within the spacing group are themselves connected by chemical bonds. Among the preferred spacers are straight or branched, saturated or unsaturated, carbon chains. Theses carbon chains may also include one or more heteroatoms within the chain or at termini of the chains. By "heteroatoms" is meant atoms other than carbon which are chosen from the group consisting of oxygen, nitrogen and sulfur. Spacing groups may also include cyclic or aromatic groups as part of the chain or as a substitution on one of the atoms in the chain.

The number of atoms in the spacing group is determined by counting the atoms other than hydrogen. The number of atoms in a chain within a spacing group is determined by counting the number of atoms other than hydrogen along the shortest route between the substructures being connected. A functional linking group may be used to activate, e.g., provide an available functional site on, a hapten or spacing group for synthesizing a conjugate of a hapten with a label or carrier or polyamine polymer.

An "immunogenic carrier," as the terms are used herein, is an immunogenic substance, commonly a protein or a protein modified to carry a reactive thiol or amino group, that can join with a hapten, in this case doxorubicin, thereby enabling these hapten derivatives to induce an immune response and elicit the production of antibodies that can bind specifically with these haptens. The immunogenic carriers and the linking groups will be enumerated hereinafter in this application. Among the immunogenic carrier substances are included proteins, glycoproteins, complex polyamino-polysaccharides, particles, and nucleic acids that are recognized as foreign and thereby elicit an immunologic response from the host. The polyamino-polysaccharides may be prepared from polysaccharides using any of the conventional means known for this preparation.

Also various protein types may be employed as a poly (amino acid) immunogenic carrier. These types include albumins, serum proteins, lipoproteins, etc. Illustrative proteins include bovine serum albumin (BSA), keyhole limpet hemocyanin (KLH), egg ovalbumin, bovine thyroglobulin (BTG) etc. Alternatively, synthetic poly(amino acids) may be utilized. Alternatively these proteins can be modified so as to contain a reactive thiol group.

Immunogenic carriers can also include poly aminopolysaccharides, which are a high molecular weight polymer built up by repeated condensations of monosaccharides. Examples of polysaccharides are starches, glycogen, cellulose, carbohydrate gums such as gum arabic, agar, and so forth. The polysaccharide may also contain polyamino acid residues and/or lipid residues.

The immunogenic carrier can also be a poly(nucleic acid) either alone or conjugated to one of the above mentioned poly(amino acids) or polysaccharides.

The immunogenic carrier can also include solid particles. The particles are generally at least about 0.02 microns (μm) and not more than about 100 μm, and usually about 0.05 μm to 10 μm in diameter. The particle can be organic or inorganic, swellable or non-swellable, porous or non-porous, optimally of a density approximating water, generally from about 0.7 to 1.5 g/mL, and composed of material that can be transparent, partially transparent, or opaque. The particles can be biological materials such as cells and microorganisms, including non-limiting examples such as erythrocytes, leukocytes, lymphocytes, hybridomas, *Streptococcus, Staphylococcus aureus, E. coli,* and viruses. The particles can also be comprised of organic and inorganic polymers, liposomes, latex, phospholipid vesicles, or lipoproteins.

"Poly(amino acid)" or "polypeptide" is a polyamide formed from amino acids. Poly(amino acids) will generally range from about 2,000 molecular weight, having no upper molecular weight limit, normally being less than 10,000,000 and usually not more than about 600,000 daltons. There will usually be different ranges, depending on whether an immunogenic carrier or an enzyme is involved.

A "peptide" is any compound formed by the linkage of two or more amino acids by amide (peptide) bonds, usually a polymer of α-amino acids in which the α-amino group of each amino acid residue (except the $NH_2$ terminus) is linked to the α-carboxyl group of the next residue in a linear chain. The terms peptide, polypeptide and poly(amino acid) are used synonymously herein to refer to this class of compounds without restriction as to size. The largest members of this class are referred to as proteins. These polymer peptides can be modified by conventional means to convert the reactive $NH_2$ terminal group into a terminal SH group.

A "label," "detector molecule," or "tracer" is any molecule which produces, or can be induced to produce, a detectable signal. The label can be conjugated to an analyte, immunogen, antibody, or to another molecule such as a receptor or a molecule that can bind to a receptor such as a ligand, particularly a hapten. Non-limiting examples of labels include radioactive isotopes, enzymes, enzyme fragments, enzyme substrates, enzyme inhibitors, coenzymes, catalysts, fluorophores, dyes, chemiluminescers, luminescers, or sensitizers; a non-magnetic or magnetic particle, a solid support, a liposome, a ligand, or a receptor.

The term "antibody" refers to a specific protein binding partner for an antigen and is any substance, or group of substances, which has a specific binding affinity for an antigen to the exclusion of other substances. The generic term antibody subsumes polyclonal antibodies, monoclonal antibodies and antibody fragments.

The term "derivative" refers to a chemical compound or molecule made from a parent compound by one or more chemical reactions.

The term "carrier" refers to solid particles and/or polymeric polymers such as immunogenic polymers such as those mentioned above. Where the carrier is a solid particle, the solid particle may be bound, coated with or otherwise attached to a polyamine polymer to provide one or more reactive sites for bonding to the functional group X in the compounds of the formula II-A and II-B.

The term "reagent kit," or "test kit," refers to an assembly of materials that are used in performing an assay. The reagents can be provided in packaged combination in the same or in separate containers, depending on their cross-reactivities and stabilities, and in liquid or in lyophilized form. The amounts and proportions of reagents provided in the kit can be selected so as to provide optimum results for a particular application. A reagent kit embodying features of the present invention comprises antibodies specific for doxorubicin. The kit may further comprise ligands of the analyte and calibration and control materials. The reagents may remain in liquid form or may be lyophilized.

The phrase "calibration and control materials" refers to any standard or reference material containing a known amount of a drug to be measured. The concentration of drug is calculated by comparing the results obtained for the unknown specimen with the results obtained for the standard. This is commonly done by constructing a calibration curve.

The term "biological sample" includes, but is not limited to, any quantity of a substance from a living thing or formerly living thing. Such living things include, but are not limited to, humans, mice, monkeys, rats, rabbits, horses, and other animals. Such substances include, but are not limited to, blood, serum, plasma, urine, cells, organs, tissues, bone, bone marrow, lymph, lymph nodes, synovial tissue, chondrocytes, synovial macrophages, endothelial cells, and skin.

Reagents and Immunogens

In constructing an immunoassay, a conjugate of doxorubicin is constructed to compete with the doxorubicin in the sample for binding sites on the antibodies. In the immunoassay of this invention, the reagents are the 13-substituted doxorubicin derivatives of the compounds of formula III-A and the 14-substituted doxorubicin derivatives of formula III-B. In the compounds of formula III-A and III-B, the linker spacer constitutes the —$CH_2$—$(Y)_p$—X'— or —B—$(Y)_p$—X' portion of this molecule. In these linkers X' and the spacer —$CH_2$—$(Y)_p$— or —B—$(Y)_p$—X' are conventional in preparing conjugates and immunogens. Any of the conventional spacer-linking groups utilized to prepare conjugates and immunogens for immunoassays can be utilized in the compounds of formula III-A and III-B. Such conventional linkers and spacers are disclosed in U.S. Pat. No. 5,501,987 and U.S. Pat. No. 5,101,015.

Among the preferred spacer groups are included the spacer groups hereinbefore mentioned. Particularly preferred spacing groups are groups such as alkylene containing from 1 to 10 carbon atoms,

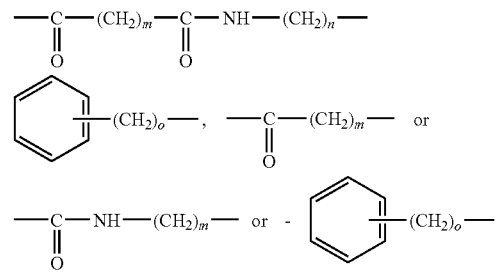

wherein n and o are integers from 0 to 6, and m is an integer from 1 to 6 with alkylene being the especially preferred spacing group. With respect to the above structures of the spacing group designated by Y, the functional group X is connected at the terminal position at the right side of the structure i.e. where $(CH_2)m$ and $(CH_2)o$ are located.

In the compounds of formula III-A and III-B, X' is —$CH_2$— or a functional group linking the spacer, to an amine or thiol group on the polymeric carrier. The group X' is the result of the terminal functional group X' in the compounds of Formula II-A and II-B which is capable of binding to the amino or thiol group in the polyamine polymer used as either the carrier or the immunogen. Any terminal functional group capable of reacting with an amine or thiol group can be utilized as the functional group X in the compounds of formula II-A and II-B. These terminal functional groups preferably included within X are:

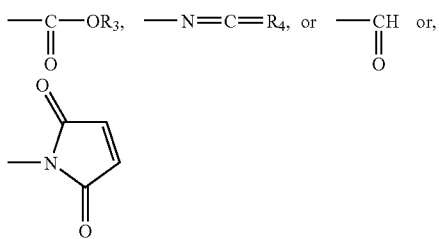

wherein $R_3$ is hydrogen or taken together with its attached oxygen atom forms a reactive ester and $R_4$ is oxygen or sulfur. The radical —N═C═$R_4$, can be an isocyanate or as isothiocyanate. The active esters formed by $OR_3$ include imidoester, such as N-hydroxysuccinamide, 1-hydroxy benzotriazole and p-nitrophenyl ester. However any active ester which can react with an amine or thiol group can be used.

The carboxylic group and the active esters are coupled to the carrier or immunogenic polymer by conventional means. The amine group on the polyamine polymer, such as a protein, produces an amide group which connects the spacer to the polymeric immunogens or carrier to form the conjugates of this invention.

When X in the compound of formula II-A or II-B is

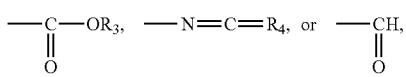

these compounds preferably react with the free amino group of the polymeric or immunogenic carrier. On the other hand, when X in the compound of formula II-A or II-B is the maleimide radical of the formula

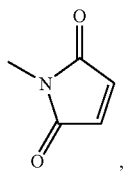

this compound preferably reacts with the thiol (or SH) group which may be present on the polymeric or protein carrier, including the immunogens, to produce X' in the compounds of the formula III-A and III-B having the structure:

III-A1

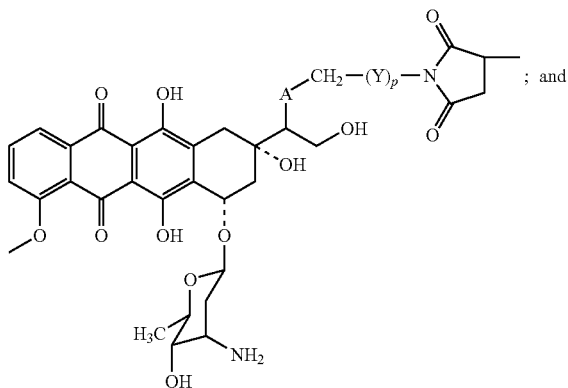

; and

III-B1

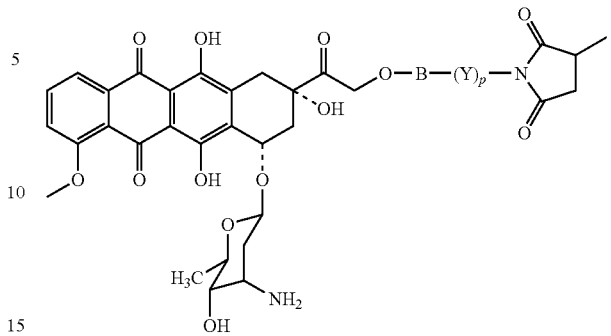

In accordance with a preferred embodiment, these compounds of formula III-A1 and III-B1 are attached to a polymeric protein which has been modified to convert an amino group to a thiol group. This can be done by the reacting a free amino group of a polymeric protein carrier with a compound of the formula

V

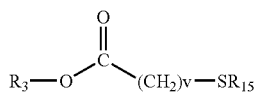

wherein $R_{15}$ is a thiol protecting group;
$R_3$ is as above; and
v is an integer of from 1 to 4.

In this manner, the thiol group, SH— becomes the functional group of the carrier bonded to the remainder of the carrier.

This reaction is carried out in an aqueous medium by mixing the protein containing carrier with the compound of formula V in an aqueous medium. In this reaction temperature and pressure are not critical and the reaction can be carried out at room temperature and atmospheric pressure. Temperatures of from 10° C. to 25° C. are generally preferred. In the next step before the thiol modified carrier is reacted with the compound of formula II-A and II-B after the thiol protecting group of carrier is removed by conventional means from the resulting reaction product of the compound of formula V with the carrier.

Any conventional means for removing a thiol protecting group can be utilized in carrying out this reaction. However, in utilizing a means to remove the thiol protecting group, care must be taken that the reactants be soluble in the aqueous medium and do not in any way destroy or harm the polyamine polymer contained in the carrier. A preferred means for removing this protecting group is by the use of dithiothreitol as an agent to reduce the resultant condensation product. This reduction can be carried out by simply adding the reducing agent to the reaction medium without utilizing higher pressures or temperatures. This reduction can be carried out at room temperature and atmospheric pressure. Any conventional thiol protecting agent can be utilized in carrying out this in the compound of formula V. The thiol protecting groups are well known in the art with 2-pyridyldithio being the preferred protecting group.

While the above method represents one means for converting a reactive terminal amino group on the polyamine polymeric containing carrier to a thiol group, any conventional means for carrying out this conversion can be utilized. Methods for converting terminal amino groups on polyamine polymeric containing carriers are well known in the art and can be employed in accordance with this invention.

It has been found that in accordance with the preferred embodiment of this invention, when the compounds of formula III-A and III-B having X' bound to a thiol group carried by the immunogenic polymeric polyamine containing carrier produce antibodies of greater specificity to doxorubicin. Therefore, the use of the compound of formula II-A and II-B where X is bonded to a terminal thiol group of the immunogenic polymeric polyamine polymeric containing carrier constitutes the preferred embodiment of the immunogens of this invention.

The reaction of the polymeric polyamine containing carrier having a terminal reactive thiol group with the compound of formula II-A or II-B where X is a functional group capable of binding to the terminal thiol group carried by the carrier can be carried out by conventional means. In the preferred embodiment the maleimide of formula III-A1 and III-B1 is reacted with the thiol group carried by the polyamine polymeric carrier.

Any well known means for addition of a thiol across a maleimide double bond can be utilized in producing the conjugates of formula II-A and II-B which are conjugated through a thiol bridge.

In the conjugates, bonded through amide bonds which conjugates include the immunogens of the present invention, the chemical bond between the carboxyl group containing doxorubicin haptens and the amino groups on the carrier or immunogen can be obtained using a variety of methods known to one skilled in the art. It is frequently preferable to form amide bonds by first activating the carboxylic acid moiety of the doxorubicin hapten in the compounds of formula II-A and II-B by reacting the carboxy group with a leaving group reagent (e.g., N-hydroxysuccinimide, 1-hydroxybenzotriazole, p-nitrophenol and the like). An activating reagent such as dicyclohexylcarbodiimide, diisopropylcarbodiimide and the like can be used. The activated form of the carboxyl group in the doxorubicin hapten of formula II-A or II-B is then reacted in a buffered solution containing the protein carrier.

In preparing the amino bonded conjugates where the doxorubicin derivative of formula II-A or II-B contains a primary or secondary amino group as well as the carboxyl group, it is necessary to use an amine protecting group during the activation and coupling reactions to prevent the conjugates from reacting with themselves. Typically, the amines on the doxorubicin derivative of formula II-A or II-B are protected by forming the corresponding N-trifluoroacetamide, N-tertbutyloxycarbonyl urethane (N-t-BOC urethane), N-carbobenzyloxy urethane or similar structure. Once the coupling reaction to the immunogenic polymer or carrier has been accomplished, as described above, the amine protecting group can be removed using reagents that do not otherwise alter the structure of the immunogen or conjugate. Such reagents and methods are known to one skilled in the art and include weak or strong aqueous or anhydrous acids, weak or strong aqueous or anhydrous bases, hydride-containing reagents such as sodium borohydride or sodium cyanoborohydride and catalytic hydrogenation. Various methods of conjugating haptens and carriers are also disclosed in U.S. Pat. No. 3,996,344 and U.S. Pat. No. 4,016,146, which are herein incorporated by reference.

On the other hand in preparing amino conjugates where X is a terminal isocyanate or thioisocyanate radical in the compound of formula II-A or II-B, these radicals when reacted with the free amine of a polyamine polymer produce the conjugate or immunogen of formula III-A or III-B where X' is

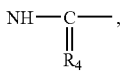

where $R_4$ is as above, which functionally connects with the amino group on the polyamine carrier or the immunogenic polypeptide.

In preparing the amino conjugates of the compounds of formula II-A and II-B, where X is an aldehyde group these compounds may be connected to the amine group of the polyamine polypeptide or carrier through an amine linkage by reductive amination. Any conventional method of condensing an aldehyde with an amine such as through reductive amination can be used to form this linkage. In this case, X' in the ligand portions of formula III-A and III-B is —$CH_2$—.

Doxorubicin of the compound of formula I, and its 13-keto group can be represented by the formula:

where

represents doxorubicin with its 13-keto group shown. The 13-keto doxorubicin can be converted to the compound of formula II-A where A is =N—O— by reacting doxorubicin with a methoxyamine of the formula:

          VI-A to produce the compound of the formula:

VI-B
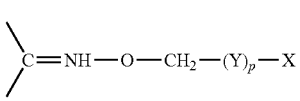

wherein p, Y and X are as above.

The compound of formula I is reacted at its 13-oxo group with a methoxyamine of formula VI-A to form the compounds of formula VI-B by conventional means of condensing methoxyamine with a carbonyl group to form an oxylamine of formula VI-B such as disclosed in U.S. Pat. No. 4,039,385. If the compound of formula VI-A contains any functional substituents, these substituents can be reacted with conventional protecting groups prior to the reaction of doxorubicin with a compound of VI-A. After the conjugate is produced from the compound of formula VI-B, these protecting groups can be removed by procedures well known in the art for removing such protecting groups while retaining the oxylamine linkage in the compound of formula VI-B.

The compound of formula II-A where A is

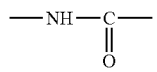

can be prepared by first converting the 13-oxo group on doxorubicin to 13-amino group and then condensing this 13-amino doxorubicin with an acid halide of the formula:

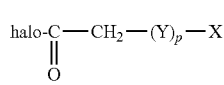  VIII-A wherein Y, p and X are as above.

The 13-oxo group on doxorubicin can be converted to the 13-amino group by reductive amination utilizing ammonium chloride and a reducing agent such as sodium cyanoborohydride.

Any of the conditions conventional in reductive amination can be utilized to convert the 13-oxo group on doxorubicin to an amino group. The 13-amino doxorubicin is reacted with the acid halide by condensation to form the amide of formula II-A where A is

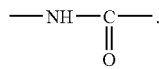

Any method of condensing an acid halide with an amine to form an amide can be utilized to carry out his condensation.

The compound of formula II-A where A is a hydrazone of the formula

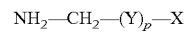

can be prepared by reacting the 13-oxo in the doxorubicin of formula I with a hydrazide of the formula

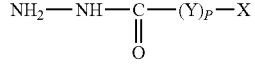  IX-B where p, Y and X are as above.

Any method of reacting a ketone with a hydrazide to produce a hydrazone can be used to carry out this conversion. Generally this reaction is carried out by reacting the ammonium salt of the compound of IX-B with the 13-oxo group on the compound of formula I, in an inert organic solvent medium such as a lower alkanol at a pH of from 3 to 6, with acid pHs being generally preferred. In carrying out this reaction temperature and pressure are not critical and this reaction can be carried out at room temperature and atmospheric pressure.

The 14-substituted compounds of formula II-B where B is —CH$_2$— are formed by reacting the 14-hydroxy group of doxorubicin with a halide of the formula:

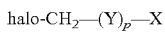  VIII-B wherein p, Y and X are as above.

In forming the compound of formula II-B from doxorubicin, any conventional means of reacting an alcohol to form an ether can be utilized to condense the compound of formula VIII-B with the 14-hydroxy position on the doxorubicin. The use of a halide in the compound of formula VIII-B provides an efficient means for forming such an ether by condensing with the alcohol. On the other hand, where Y in the compound of formula VIII-B contains functional groups, which may interfere with this reaction to form the compound of formula II-B, these functional groups can be protected by means of suitable protecting groups which can be removed after this reaction as described hereinabove.

The 14-substituted compounds of formula II-B where B is

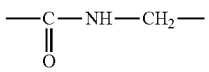

is produced by reacting 14-hydroxy group on doxorubicin with an amino compound of the formula:

$$NH_2—CH_2—(Y)_p—X \qquad \text{IX}$$

wherein X, Y and p are as above.

After first converting the 14-hydroxy group on doxorubicin to the chloroformatic group

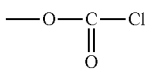

Any conventional means of converting a hydroxy group to a chloroformatic group can be used. After the formulation of a chloroformate, the halo group of the chloroformate is condensed with the amine group in the compound of formula IX. Prior to this reaction, the reactive group on doxorubicin and/or on the compound of formula IX are protected as described hereinabove with a conventional protecting group. These protecting groups can be removed after this halide condensation by conventional means such as described hereinbefore.

The compound of formula II-A and II-B can be converted into the immunogens and/or the conjugate reagents of this invention by reacting these compounds with a polyamine or a polypeptide carrier which contains a terminal amino group. The same polypeptide can be utilized as the carrier and as the immunogenic polymer carrier in the immunogen of this invention provided that the polyamine or polypeptide carrier used to generate the antigen is immunologically active. However, to form the conjugates, these polymers need not produce an immunological response as needed for the immunogens. In accordance with this invention, the various functional groups represented by X in the compounds of formula II-A and II-B can be conjugated to the polymeric material by conventional means of attaching a functional group to an amine or thiol group contained within the polymeric carrier.

Antibodies

The present invention also relates to novel antibodies including monoclonal antibodies to doxorubicin produced by utilizing the aforementioned immunogens. In accordance with this invention it has been found that these antibodies produced in accordance with this invention are selectively reactive with doxorubicin and unlike the prior art antibodies, do not react with non-pharmaceutically active metabolites which would interfere with immunoassays for doxorubicin. The most problematic of these doxorubicin metabolites is doxorubicin aglycone. The ability of the antibodies of this invention not to react with these inactive metabolites makes these antibodies particularly valuable in providing an immunoassay for doxorubicin.

The present invention relates to novel antibodies and monoclonal antibodies to doxorubicin. The antisera of the invention can be conveniently produced by immunizing host animals with the immunogens of this invention. Suitable host animals include rodents, such as, for example, mice, rats, rabbits, guinea pigs and the like, or higher mammals such as goats, sheep, horses and the like. Initial doses, bleedings and booster shots can be given according to accepted protocols for eliciting immune responses in animals, e.g., in a preferred embodiment mice received an initial dose of 100 ug immunogen/mouse, i.p. and one or more subsequent booster shots of between 50 and 100 ug immunogen/mouse over a six month period. Through periodic bleeding, the blood samples of the immunized mice were observed to develop an antibodies against doxorubicin utilizing conventional immunoassays. These methods provide a convenient way to screen for hosts which are producing antisera having the desired activity. The antibodies were also screened against the major metabolites of doxorubicin and showed no substantial binding to these compounds.

Monoclonal antibodies are produced conveniently by immunizing Balb/c mice according to the above schedule followed by injecting the mice with 100 ug immunogen i.p. or i.v. on three successive days starting four days prior to the cell fusion. Other protocols well known in the antibody art may of course be utilized as well. The complete immunization protocol detailed herein provided an optimum protocol for serum antibody response for the antibody to doxorubicin.

B lymphocytes obtained from the spleen, peripheral blood, lymph nodes or other tissue of the host may be used as the monoclonal antibody producing cell. Most preferred are B lymphocytes obtained from the spleen. Hybridomas capable of generating the desired monoclonal antibodies of the invention are obtained by fusing such B lymphocytes with an immortal cell line, which is a cell line that which imparts long term tissue culture stability on the hybrid cell. In the preferred embodiment of the invention the immortal cell may be a lymphoblastoid cell or a plasmacytoma cell such as a myeloma cell. Murine hybridomas which produce doxorubicin monoclonal antibodies are formed by the fusion of mouse myeloma cells and spleen cells from mice immunized against doxorubicin-protein conjugates. Chimeric and humanized monoclonal antibodies can be produced by cloning the antibody expressing genes from the hybridoma cells and employing recombinant DNA methods now well known in the art to either join the subsequence of the mouse variable region to human constant regions or to combine human framework regions with complementary determining regions (CDR's) from a donor mouse or rat immunoglobulin. An improved method for carrying out humanization of murine monoclonal antibodies which provides antibodies of enhanced affinities is set forth in International Patent Application WO 92/11018.

Polypeptide fragments comprising only a portion of the primary antibody structure may be produced, which fragments possess one or more immunoglobulin activities. These polypeptide fragments may be produced by proteolytic cleavage of intact antibodies by methods well known in the art, or by inserting stop codons at the desired locations in expression vectors containing the antibody genes using site-directed mutagenesis to produce Fab fragments or (Fab')$_2$ fragments. Single chain antibodies may be produced by joining VL and VH regions with a DNA linker (see Huston et al., *Proc. Natl. Acad. Sci. U.S.*, 85:5879-5883 (1988) and Bird et al., *Science*, 242:423-426 (1988)).

The antibodies of this invention are selective for doxorubicin without having any substantial cross-reactivity with pharmaceutically active metabolites of doxorubicin such as the metabolites mentioned hereinabove. By having no substantial cross-reactivity it is meant that the antibodies of this invention have a cross reactivity relative to doxorubicin with these metabolites of less than 20%. Those antibodies having a cross reactivity of less than 15% are preferred. The antibodies of this invention may be reactive with other pharmaceutically active doxorubicin like compounds such as doxorubicinol.

Immunoassays

In accordance with this invention, the conjugates and the antibodies generated from the immunogens of these compounds of formula II-A and II-B or mixtures thereof can be utilized as reagents for the determination of doxorubicin in patient samples. This determination is performed by means of an immunoassay. Any immunoassay in which the reagent conjugates formed from the compounds of formula II-A and II-B compete with the doxorubicin in the sample for binding sites on the antibodies generated in accordance with this invention can be utilized to determine the presence of doxorubicin in a patient sample. The manner for conducting such an assay for doxorubicin in a sample suspected of containing doxorubicin, comprises combining an (a) aqueous medium sample, (b) an antibody to doxorubicin generated in accordance with this invention and (c) the conjugates formed from the compounds of formula II-A or II-B or mixtures thereof. The amount of doxorubicin in the sample can be determined by measuring the inhibition of the binding to the specific antibody of a known amount of the conjugate added to the mixture of the sample and antibody. The result of the inhibition of such binding of the known amount of conjugates by the unknown sample is compared to the results obtained in the same assay by utilizing known standard solutions of doxorubicin.

Various means can be utilized to measure the amount of conjugate formed from the compounds of formula II-A and II-B bound to the antibody. One method is where binding of the conjugates to the antibody causes a decrease in the rate of rotation of a fluorophore conjugate. The amount of decrease in the rate of rotation of a fluorophore conjugate in the liquid mixture can be detected by the fluorescent polarization technique such as disclosed in U.S. Pat. No. 4,269,511 and U.S. Pat. No. 4,420,568.

On the other hand, the antibody can be coated or absorbed on nanoparticles so that when these particles react with the doxorubicin conjugates formed from the compounds of formula II-A and II-B, these nanoparticles form an aggregate. However, when the antibody coated or absorbed nanoparticles react with the doxorubicin in the sample, the doxorubicin from the sample bound to these nanoparticles does not cause aggregation of the antibody nanoparticles. The amount of aggregation or agglutination can be measured in the assay mixture by absorbance.

On the other hand, these assays can be carried out by having either the antibody or the doxorubicin conjugates attached to a solid support such as a microtiter plate or any other conventional solid support including solid particles. Attaching antibodies and proteins to such solid particles is well known in the art. Any conventional method can be utilized for carrying out such attachments. In many cases, in order to aid measurement, labels may be placed upon the antibodies, conjugates or solid particles, such as radioactive labels or enzyme labels, as aids in detecting the amount of the conjugates formed from the compounds of formula II-A and II-B which is bound or unbound with the antibody. Other suitable labels include chromophores, fluorophores, etc.

As a matter of convenience, assay components of the present invention can be provided in a kit, a packaged combination with predetermined amounts of new reagents employed in assaying for doxorubicin. These reagents include the antibody of this invention, as well as, the conjugates formed from the compounds of formula II-A and II-B or mixtures thereof. It is generally preferred that in a given immunoassay, if a conjugate formed from a compound of formula II-A is utilized, that the antibody be generated by an immunogen formed from a compound of formula II-A. In a like manner, if a conjugate formed from a compound of formula II-B is utilized, the antibody be generated by the immunogen formed from a compound of formula II-B. However, this need not be the case and antibodies and conjugates in a given assay can be derived from either or both of these conjugates and immunogens.

In addition to these necessary reagents, additives such as ancillary reagents may be included, for example, stabilizers, buffers and the like. The relative amounts of the various reagents may vary widely to provide for concentrations in solution of the reagents which substantially optimize the sensitivity of the assay. Reagents can be provided in solution or as a dry powder, usually lyophilized, including excipients which on dissolution will provide for a reagent solution having the appropriate concentrations for performing the assay.

EXAMPLES

In the Examples, the following abbreviations are used for designating the following:
CHCl$_3$ Chloroform
BMPH N-[β-maleimidopropionic acid]hydrazide, trifluoroacetic acid salt
MeOH methanol
DMF Dimethylformamide
TFA Trifluoroacetic acid
DMSO Dimethylsulfoxide
CAPS 3-(Cyclohexylamino)-1-propanesulfonic acid
NHS N-hydroxy succinimide
EDC 1-(3-dimethylaminopropyl)-3-ethylcarbodiimide hydrochloride
KPi potassium phosphate buffer pH 7.5
SPDP 3-(2-Pyridyldithio)propionic acid N-hydroxysuccinimide ester
MES 2-(N-Morpholino)ethanesulfonic acid buffer pH 6
ANS 8-Anilino-1-naphthalenesulfonic acid
i.p. Intraperitoneal
HRP horse radish-peroxidase
TFA Trifluoroacetic
TMB 3,3',5,5'-Tetramethylbenzidine
TRIS Tris(hydroxymethyl)aminomethane hydrochloride
BSA Bovine serum albumin
KLH Keyhole Limpet Hemocyanin
BTG Bovine thyroglobulin
PBS Phosphate buffered saline
di deionized water In the Examples, Scheme 1 and Scheme 2 below set forth the specific compounds prepared and referred to by numbers in the Examples. The schemes are as follows:

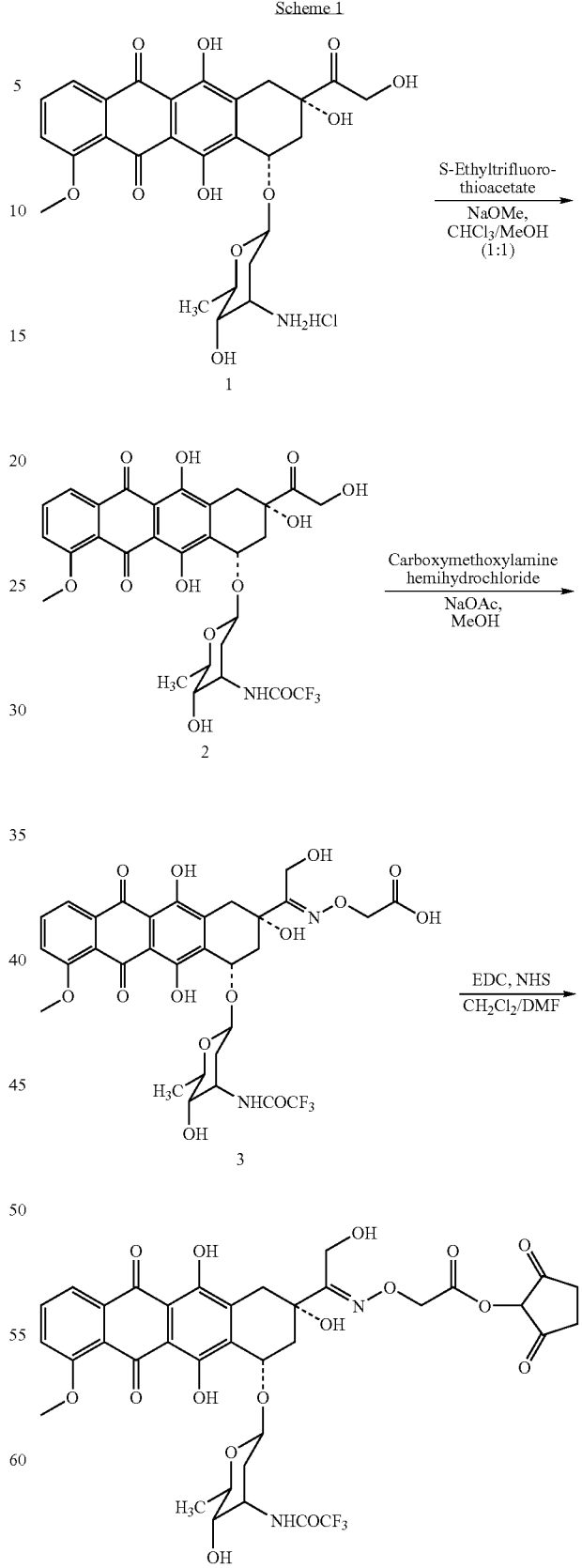

Scheme 2

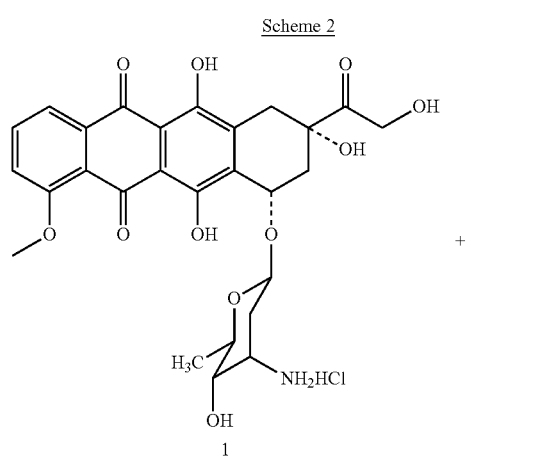

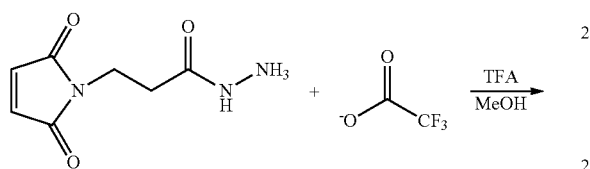

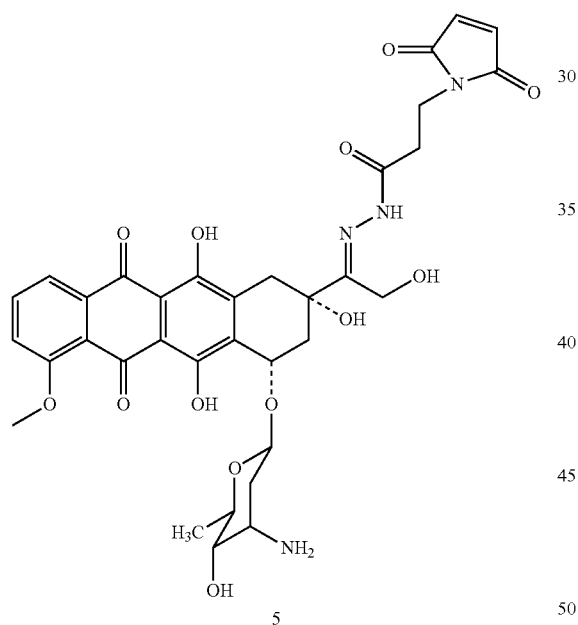

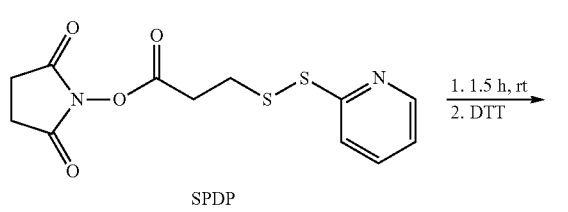

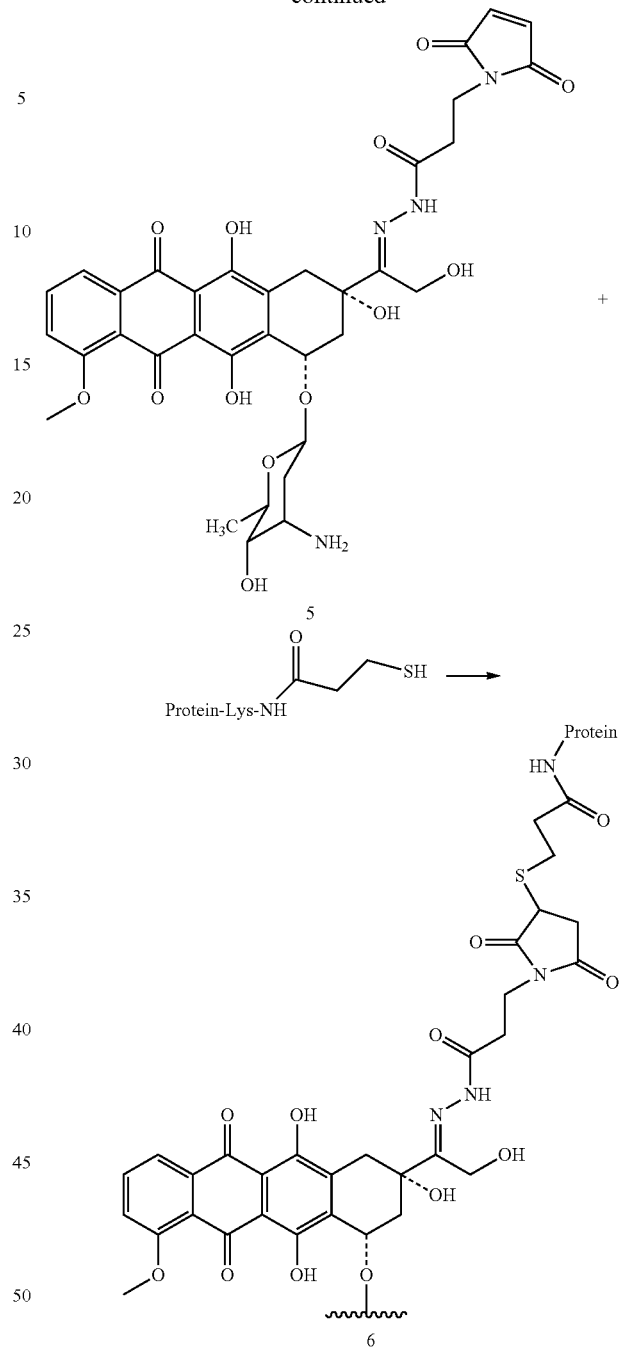

Example 1

Preparation of Doxorubicin Trifluoroacetamide Activated Ester 4 (Scheme 1)

A stirred suspension of doxorubicin (1) (0.8 g, 1.38 mmol) in $CHCl_3$/MeOH (1:1) (15 mL) at 0° C. was treated with 2.76 mL of 0.5 M methanolic sodium methoxide added dropwise followed by addition of S-ethyltrifluorothioacetate (0.89 mL, 7.02 mmol) under a nitrogen atmosphere. After being stirred in the dark for 16 h at room temperature, the reaction was concentrated in vacuo. The residue was dissolved in 10 mL of $CHCl_3$/MeOH (1:1), and 4 mL of toluene, and concentrated.

Again the residue was dissolved in 50 mL of CHCl$_3$/MeOH (9:1) and washed with 10 mL of 0.1 M citric acid, and brine (2×10 mL). It was dried over magnesium sulfate and evaporation of solvents followed by trituration in methylene chloride/Ether/Hexanes gave 2 (0.814, 92%) as a red solid.

A mixture of compound 2 (0.49 g, 0.766 mmol), carboxymethoxylamine hemihydrochloride (0.30 g, 1.38 mmol), and sodium acetate (0.38 g, 4.60 mmol) in MeOH (15 mL) was stirred in the dark overnight at room temperature. The solvent was removed under reduced pressure and the residue was dissolved in water (25 mL) and CHCl$_3$/MeOH (9:1) (3×25 mL). All the combined organic layers were dried over MgSO$_4$, evaporated, and triturated with methylene chloride/Hexanes to afford 3 (0.45 g, 82%).

To a solution of compound 3 (0.45 g, 0.63 mmol) in methylene chloride/DMF (1:5) (12 mL) at 0° C., were added EDC (0.11 g, 0.95 mmol) and NHS (0.18 g, 0.95 mmol) under a nitrogen atmosphere. After being stirred for 18 h at room temperature, the reaction mixture was diluted with methylene chloride (50 mL) and washed with water (2×15 mL). It was dried over magnesium sulfate, and evaporation of solvent gave compound 4 (0.445 g, 86%) as a red solid; this material was directly used in the next step (Examples 3a and 3b).

Example 2

Preparation of (3-Maleimidopropyl)hydrazone of Doxorubicin (Scheme 2)

Doxorubicin [1] was derivatized with N-[β-maleimidopropionic acid]hydrazide (BMPH) to introduce a maleimido group for eventual conjugation to protein through a thio-ether linkage. To a solution of doxorubicin hydrochloride (29 mg, 0.05×10−3 mmol), BMPH (50 mg, 3.4 eq.) in 10 ml of anhydrous MeOH was added 3 µL of TFA. The reaction mixture was stirred at room temperature for 24 hours while being protected from light. The methanolic solution was concentrated to a volume of 2 mL and added to acetonitrile (30 ml) dropwise with stirring. The resulting suspension was allowed to stand at 4° C. overnight for crystallization of the doxorubicin C$_{13}$ hydrazone maleimido derivative [5]. This product was isolated by centrifugation, washed with fresh methanol-acetonitrile (1:10), and dried under vacuum to yield the (6-Maleimidocaproyl) hydrazone of doxorubicin (5). The structure was confirmed by NMR.

Example 3a

Preparation of BTG Immunogen with Activated Hapten 4

To 18.8 mL of BTG (7.1 mg/mL) in 1:1 phosphate buffer (50 mM, pH 7.5):DMSO was added 1.3 mL of compound 4 from Example 1 (20 mg/mL in DMSO) while stirring the protein solution on ice. After addition the pH was again checked to be 8. The mixture was allowed to stir for 18 hours at room temperature. The trifluoroacetamide protecting group on the amino sugar was removed by dialysis with CAPS buffer, pH 11. The first dialysis was performed with 50% 50 mM CAPS and 50% DMSO at room temperature. Thereafter the DMSO proportion was reduced stepwise: 40%, 30%, 20%, 10% and 0%. For the last CAPS dialysis the buffer concentration was reduced to 25 mM and the dialysis done at 4° C. The immunogenic conjugate was then purified by dialysis against phosphate buffer (50 mM, pH 7.5). The conjugate was characterized by UV/VIS spectroscopy.

Example 3b

Preparation of KLH Immunogen with Activated Hapten 4

To 18.0 mL of KLH (7.35 mg/mL) in 1:1 phosphate buffer (50 mM, pH 7.5):DMSO was added 1.3 mL of compound 4 from Example 1 (20 mg/mL in DMSO) while stirring the protein solution on ice. After addition the pH was again checked to be 8. The mixture was allowed to stir for 18 hours at room temperature. The trifluoroacetamide protecting group on the amino sugar was removed by dialysis with CAPS buffer, pH 11. The first dialysis was performed with 50% 50 mM CAPS and 50% DMSO at room temperature. Thereafter the DMSO proportion was reduced stepwise: 40%, 30%, 20%, 10% and 0%. For the last CAPS dialysis the buffer concentration was reduced to 25 mM and the dialysis done at 4° C. The immunogenic conjugate was then purified by dialysis against phosphate buffer (50 mM, pH 7.5). The conjugate was characterized by UV/VIS spectroscopy.

Example 4a

Preparation of BTG Immunogen with Activated Hapten 5

To conjugate the doxorubicin C$_{13}$ hydrazone maleimido derivative to protein the lysine residues of the protein were modified to introduce a sulfhydryl group. To a solution of bovine thyroglobulin (BTG) in potassium phosphate buffer, pH 7.5 (14.9 mg/mL, 3 mL) was added 4 mg of 3-(2-Pyridyldithio)propionic acid N-hydroxysuccinimide ester (SPDP) (20 eq.) in 50 µL of DMSO to derivatize the lysines with propionic pyridyldithio groups. After 1.5 hours stirring at room temperature, 40 mg of dithiothreitol dissolved in 100 µL of KPi was added to the mixture to generate the sulfhydryls by reduction of the dithiopyridyl moiety. The reduction of the pyridyldithio derivative on the protein to release the sulfhydryl group was performed under nitrogen, with stirring at room temperature for 30 minutes. The thiolated BTG was then purified by gel-filtration chromatography.

The gel-filtration column was prepared with 15 g of Sephadex G-25 swelled in 50 mM KPi Buffer at room temperature for 1 h, degassed under vacuum, and loaded in a column (1.5 cm×50 cm). The loaded column was equilibrated with the buffer for 1 hour. The reaction mixture was loaded onto the column, and eluted with KPi buffer. Ellman's reagent was used to monitor the elution of the protein. The fractions containing protein were collected and pooled. The molar concentration of thiol groups was determined by the Ellman's procedure (Riddles, P. W. et al., *Analytical Biochemistry*, Ellman's reagent: 5,5'-Dithiobis(2-nitrobenzoic acid)-A reexamination, 94, 75-81 (1979).

To the purified thiolated-BTG protein (5 mg/mL in KPi, 44.7 mg) in an ice-water bath was added dropwise 3 mL of the doxorubicin hydrazone derivate 5 prepared in Example 2 (2.33 mg/mL) the reaction mixture was stirred at 4° C. for 16 hours and protected from light. The immunogenic conjugate was purified by gel-filtration as described above. The immunogenic conjugate was characterized by UV/VIS spectroscopy.

Example 4b

Preparation of KLH Immunogen with Activated Hapten 5

To a solution of KLH in potassium phosphate buffer, pH 7.5 (5.58 mg/mL, 4 mL) was added 3 mg of SPDP in 50 μL of DMSO. After 1.5 hours stirring at room temperature, 25 mg of dithiothreitol dissolved in 50 μL of KPi was added to the mixture. The reduction was performed under nitrogen, with stirring at room temperature for 30 minutes. The thiolated KLH was then purified by gel-filtration chromatography as described in Example 4a.

To the purified thiolated-KLH protein (4 mg/mL in KPi, 5 mL) in an ice-water bath was added dropwise 2.124 mL of the doxorubicin hydrazone derivative 5 prepared in Example 2 (1.41 mg/mL) the reaction mixture was stirred at 4° C. for 16 hours and protected from light. The immunogenic conjugate was purified by gel-filtration as described in Example 4a. The immunogenic conjugate was characterized by IN/VIS spectroscopy.

Example 5

Preparation of BSA Conjugate (1:1 ratio) with Activated Hapten 4

To 40 mL of BSA (25 mg/mL) in 1:1 phosphate buffer (50 mM, pH 7.5):DMSO was added 0.62 mL of compound 4 from Example 1 (20 mg/mL in DMSO) while stirring the protein solution on ice. After addition the pH was again checked to be 8. The mixture was allowed to stir for 18 hours at room temperature. The trifluoroacetamide protecting group on the amino sugar was removed by dialysis with CAPS buffer, pH 11. The first dialysis was performed with 50% 50 mM CAPS and 50% DMSO at room temperature. Thereafter the DMSO proportion was reduced stepwise: 40%, 30%, 20%, 10% and 0%. For the last CAPS dialysis the buffer concentration was reduced to 25 mM and the dialysis done at 4° C. The immunogenic conjugate was then purified by dialysis against phosphate buffer (50 mM, pH 7.5). The conjugate was characterized by UV/VIS spectroscopy.

Example 6a

Preparation of Thiolated BSA for Reaction with Activated Hapten 5

To a solution of BSA in potassium phosphate buffer, pH 7.5 (50 mg/mL, 6 mL) was added 4.2 mg of SPDP (3 eq.) in 84 μL of DMSO. After 1.5 hours stirring at room temperature, 27 mg of dithiothreitol dissolved in 0.135 mL of KPi was added to the mixture. The reduction was performed under nitrogen, with stirring at room temperature for 30 minutes. The thiolated BSA was then purified by gel-filtration chromatography.

The gel-filtration column was prepared with 12 g of Sephadex G-25 swelled in 10 mM MES Buffer (pH 6) at room temperature for 1 h, degassed under vacuum, and loaded in a column (1.5 cm×50 cm). The loaded column was equilibrated with the buffer for 1 hour. The reaction mixture was loaded onto the column, and eluted with MES buffer. Ellman's reagent was used to monitor the elution of the protein. The fractions containing protein were collected and pooled. The molar concentration of thiol groups was determined by the Ellman's procedure.

Example 6b

Preparation of BSA Conjugate (3:1 ratio) with Activated Hapten 5

To the purified thiolated-BSA protein prepared in Example 6a (5 mg/mL in MES, 35 mg) in an ice water bath was added dropwise 0.135 mL of the doxorubicin hydrazone derivate 5 prepared in Example 2 (8 mg/mL) the reaction mixture was stirred at 4° C. for 16 hours and protected from light. The immunogenic conjugate was purified by gel-filtration as described in Example 6a. The immunogenic conjugate was characterized by UV/VIS spectroscopy.

Example 6c

Preparation of BSA Conjugate (1:1 Ratio) with Activated Hapten 5

To the purified thiolated-BSA protein prepared in Example 6a (5 mg/mL in MES, 80 mg) in an ice water bath was added dropwise 0.107 mL of the doxorubicin hydrazone derivate 5 prepared in Example 2 (8 mg/mL) the reaction mixture was stirred at 4° C. for 16 hours and protected from light. The immunogenic conjugate (6 mL) was purified by gel-filtration as described in Example 6a. The purified immunogenic conjugate was characterized by TV/VIS spectroscopy. The rest of immunogenic conjugate reaction mixture was used for the capping reaction without further purification.

Example 6d

Capping of Doxorubicin Hydrazone 5-BSA Conjugate (1:1 Ratio)

To 5 mL of 1:1 doxorubicin [5]-BSA conjugate prepared in Example 6c (5 mg/mL in MES buffer) was added 0.047 mL of N-Ethylmaleimide (2 equivalents, 2 mg/mL in MES buffer) to cap thiol groups not modified by doxorubicin. The reaction was stirred for 3 hours at room temperature and then purified as in Example 6a.

Example 7

Preparation of Doxorubicin [4] Antibodies

Two groups of ten Female BALB/c mice were immunized i.p. one with 100 μg/mouse of doxorubicin [4]-BTG immunogen prepared in Example 3a and the other with 100 μg/mouse of doxorubicin [4]-KLH immunogen prepared in Example 3b emulsified in Complete Freund's adjuvant. The mice were boosted once four weeks after the initial injection with 100 μg/mouse of the same immunogens emulsified in Incomplete Freund's Adjuvant. Ten days after the boost test bleeds from each mouse were obtained by orbital bleed. For monoclonal antibodies depending on the immunogen, age and rest period of the mouse starting four days before the fusion, the mice were injected i.p. with either 400 μg (3 days before fusion), 200 μg (2 days before fusion), and 200 μg (1 day before fusion) of doxorubicin [4]-BTG immunogen prepared in Example 3a in PBS or 100 ug on each day of doxorubicin [4]-KLH immunogen prepared in Example 3b in PBS on three successive days. According to the protocol of Coligan et al. spleen cells were isolated from the selected mice and fused with 2×10[7] cells of the myeloma fusion partner cell line (SP2/0) using 50% polyethylene glycol 1500 [Coligan, J. E. et al., eds., *Current Protocols in Immunology*, 2.5.1-2.5.8, (1992), Wiley & Sons, NY.] To grow the fused cells into antibody producing colonies according to the method of Coligan et al. the fused cells were plated on 10 96-well plates in a conventional HAT (hypoxanthine, aminopterin and thymidine) selective growth medium such as DMEM/F12 (Dulbecco's Modified Eagle's Medium 1:1 with L-glutamine and HEPES) supplemented with 20% fetal bovine serum alternative, and containing 2% L-glutamine (100 mM) and 2% 50×HAT. Two weeks later, the hybridoma supernatant was assayed for the presence of anti-doxorubicin antibodies by ELISA as described in Example lob. Positive wells were expanded and again screened by the same method. The positive clones were confirmed for doxorubicin binding by a competitive ELISA as described in Example 11 or subcloned directly. Clones positive by ELISA were subcloned once or twice by limiting dilution according to the method disclosed in Coligan, J. E. et al., eds., *Current Protocols in Immunology*, 2.5.8-2.5.17, (1992), Wiley & Sons, NY. Only the monoclonal antibodies which were selective for doxorubicin and had a cross reactivity relative to doxorubicin with the aglycone of doxorubicin of 15% or less as determined by these screening procedures were selected.

Example 8

Preparation of Doxorubicin [5] Antibodies

Two groups of ten Female BALB/c mice were immunized i.p. one group with 100 µg/mouse of doxorubicin [5]-BTG immunogen prepared in Example 4a and the other with 100 µg/mouse doxorubicin [5]-KLH immunogen prepared in Example 4b emulsified in Complete Freund's Adjuvant. Mice were boosted once four weeks after the initial injection with 100 µg/mouse of the same immunogens emulsified in Incomplete Freund's Adjuvant. Ten and 28 days after the boost test bleeds from each mouse were obtained by orbital bleed. The anti-serum from the day 28 test bleeds contained doxorubicin antibodies evaluated in Examples 10a and 11. Only the anti-serum having antibodies which were selective for doxorubicin and had a cross reactivity relative to doxorubicin with the aglycone of doxorubicin of 15% or less as determined by these screening procedures were selected.

Example 9a

Microtiter Plate Sensitization Procedure with Doxorubicin [4]-BSA 1:1 Conjugate

For the purpose of screening antibodies and measuring doxorubicin concentration by the Enzyme-Linked Immunosorbent Assay (ELISA) method polystyrene microtiter plates (Nunc MaxiSorp F8 Immunomodules) optimized for protein binding and containing 96 wells per plate were used. Each well was coated with doxorubicin [4]-BSA 1:1 conjugate (prepared as in Example 5) by adding 300 µL of doxorubicin [4]-BSA conjugate at 10 µg/mL in 0.01M MES, pH=6, and incubating for three hours at room temperature. The wells were washed with 0.005M MES, pH 6 and then were blocked with 375 µL of 5% sucrose, 0.2% sodium caseinate solution for 30 minutes at room temperature. After removal of the post-coat solution the plates were dried at 37° C. overnight.

Example 9b

Microtiter Plate Sensitization Procedure with Doxorubicin [5]-BSA 3:1 Conjugate

For the purpose of screening antibodies and measuring doxorubicin concentration by the Enzyme-Linked Immunosorbent Assay (ELISA) method polystyrene microtiter plates (Nunc MaxiSorp F8 Immunomodules) optimized for protein binding and containing 96 wells per plate were used. Each well was coated with doxorubicin [5]-BSA 3:1 conjugate (prepared as in Example 6b) by adding 300 µL of doxorubicin [1]-BSA conjugate at 10 µg/mL in 0.01M MES, pH=6, and incubating for three hours at room temperature. The wells were washed with 0.005M MES, pH 6 and then were blocked with 375 µL of 5% sucrose, 0.2% sodium caseinate solution for 30 minutes at room temperature. After removal of the post-coat solution the plates were dried at 37° C. overnight.

Example 9c

Microtiter Plate Sensitization Procedure with Doxorubicin [5]-BSA 1:1 Conjugate

For the purpose of screening antibodies and measuring doxorubicin concentration by the Enzyme-Linked Immunosorbent Assay (ELISA) method polystyrene microtiter plates (Nunc MaxiSorp F8 Immunomodules) optimized for protein binding and containing 96 wells per plate were used. Each well was coated with doxorubicin [1]-BSA 1:1 conjugate (prepared as in Example 6c) by adding 300 µL of doxorubicin [5]-BSA conjugate at 10 µg/mL in 0.01M MES, pH=6, and incubating for three hours at room temperature. The wells were washed with 0.005M MES, pH 6 and then were blocked with 375 µL of 5% sucrose, 0.2% sodium caseinate solution for 30 minutes at room temperature. After removal of the post-coat solution the plates were dried at 37° C. overnight.

Example 9d

Microtiter Plate Sensitization Procedure with Doxorubicin [5]-BSA 1:1 Conjugate (Thiol Capped)

For the purpose of screening antibodies and measuring doxorubicin concentration by the Enzyme-Linked Immunosorbent Assay (ELISA) method polystyrene microtiter plates (Nunc MaxiSorp F8 Immunomodules) optimized for protein binding and containing 96 wells per plate were used. Each well was coated with doxorubicin [5]-BSA 1:1 capped conjugate (prepared as in Example 6d) by adding 300 µL of doxorubicin [5]-BSA conjugate at 10 µg/mL in 0.01M MES, pH=6, and incubating for three hours at room temperature. The wells were washed with 0.005M MES, pH 6 and then were blocked with 375 µL of 5% sucrose, 0.2% sodium caseinate solution for 30 minutes at room temperature. After removal of the post-coat solution the plates were dried at 37° C. overnight.

Example 10a

Antibody Screening Procedure

Titer

Antibodies were screened by Enzyme-Linked Immunosorbent Assay (ELISA) method. This method for screening the doxorubicin antibodies (produced in Examples 7 and 8) was performed with the microtiter plates that were sensitized with doxorubicin [5]-BSA prepared in Examples 9b, c, d. The antibody screening assay was performed by diluting the antisera containing doxorubicin antibodies to 1:1,000, 1:10,000, 1:100,000 and 1:1,000,000 in phosphate buffered saline containing 0.1% BSA and 0.01% thimerosal. For evaluation of monoclonal antibodies, hybridoma supernatants, of Example 7 found to be positive for presence of antibodies by the procedure of Example 10b, were diluted 1:2, 1:4, 1:8, 1:16, etc. To each well of doxorubicin [5]-BSA sensitized wells (prepared in Examples 9b, c, d) 100 μL of diluted antibody was added and incubated for 10 minutes at room temperature with shaking. During this incubation antibody binds to the doxorubicin [5]-conjugate in the well. The wells of the plates were washed three times with 0.02 M TRIS, 0.9% NaCl, 0.5% Tween-80 and 0.001% Thimerosal, pH 7.8 to remove any unbound antibody. To detect the amount of doxorubicin antibody bound to the doxorubicin [5]-BSA conjugate in the wells, 1000 μL of a goat anti-mouse antibody—HRP enzyme conjugate (Jackson Immunoresearch) diluted to a specific activity (approximately 1/2800) in PBS with 0.1% BSA, 0.05% ANS, 0.01% thimerosal, capable of binding specifically with murine immunoglobulins and producing a colored product when incubated with a substrate, were added to each well. After an incubation of 10 minutes at room temperature with shaking, during which the goat anti-mouse antibody—HRP enzyme conjugate binds to doxorubicin antibodies in the wells, the plates were again washed three times to remove unbound goat anti-mouse antibody—HRP enzyme conjugate. To develop a measurable color in the wells washing was followed by the addition of 100 μL of TMB (TMB Liquid Substrate), a substrate for HRP, to develop color during a 10 minute incubation with shaking at room temperature. Following the incubation for color development, 50 μL of stop solution (1.5% sodium fluoride in di $H_2O$) was added to each well to stop the color development and after 10 seconds of shaking the absorbance was determined at 650 nm with a 96-well plate reader. The amount of antibody in a well was proportional to the absorbance measured and was expressed as the dilution (titer) resulting in an absorbance of 1.5. Titers were determined by graphing log antibody dilution of the antibody measured (x-axis) vs. absorbance 650 nm (y-axis) and extrapolating the titer at an absorbance of 1.5. The titer determined the concentration (dilution) of antibody used in the indirect competitive Microtiter plate assay described in Example 11.

Example 10b

Antibody Screening Procedure

Monoclonal Screening

Antibodies were screened by Enzyme-Linked Immunosorbent Assay (ELISA) method. This method for screening doxorubicin monoclonal antibodies (produced in Example 7) was performed with the microtiter plates that were sensitized with doxorubicin [1]-BSA as described in Example 9b. To each well of doxorubicin [5]-BSA sensitized wells (prepared in Example 9b) 50 μL phosphate buffered saline containing 0.1% BSA and 0.01% thimerosal and then 50 μL of monoclonal culture supernatant were added and incubated for 10 minutes at room temperature with shaking. During this incubation antibody binds to the doxorubicin [5]-conjugate in the well. The wells of the plates were washed three times with 0.02 M TRIS, 0.9% NaCl, 0.5% Tween-80 and 0.001% Thimerosal, pH 7.8 to remove any unbound antibody. To detect the amount of doxorubicin antibody bound to the doxorubicin [5]-BSA conjugate in the wells, 100 μL of a goat anti-mouse antibody—HRP enzyme conjugate (Jackson Immunoresearch) diluted to a predetermined specific activity (approximately 1/2800) in PBS with 0.1% BSA, 0.05% ANS, 0.01% thimerosal, capable of binding specifically with murine immunoglobulins and producing a colored product when incubated with a substrate, were added to each well. After an incubation of 10 minutes at room temperature with shaking, during which the goat anti-mouse antibody—HRP enzyme conjugate binds to doxorubicin antibodies in the wells, the plates were again washed three times to remove unbound goat anti-mouse antibody—HRP enzyme conjugate. To develop a measurable color in the wells washing was followed by the addition of 100 μL of TMB (TMB Liquid Substrate), a substrate for HRP, to develop color during a 10 minute incubation with shaking at room temperature. Following the incubation for color development, 50 μL of stop solution (1.5% sodium fluoride in di $H_2O$) was added to each well to stop the color development and after 10 seconds of shaking the absorbance was determined at 650 nm with a 96-well plate reader. The amount of antibody in a well was proportional to the absorbance measured. Samples with an absorbance of greater than three or more times background were designated as positive.

Example 11

Indirect Competitive Microtiter Plate Immunoassay Procedure Determining $IC_{50}$ and Cross-Reactivity for Antibodies to Doxorubicin Doxorubicin concentrations were measured by an indirect competitive Enzyme-Linked Immunosorbent Assay (ELISA) method This method for measuring doxorubicin concentrations was performed with the microtiter plates that were sensitized with doxorubicin [5]-BSA described in Examples 9b, c, d. Doxorubicin, and doxorubicin aglycone diluted 10 fold in PBS containing 0.1% BSA and 0.01% Thimerosal over a concentration range of 0.01 to 10,000 ng/mL. The assay was performed by incubating 50 μL of the analytes to be measured with 50 μL of antibody (produced in Examples 7 and 8 with immunogens of Examples 3a, 3b, 4a and 4b) diluted to a titer determined in Example boa. During the 10 minute incubation (R.T., with shaking) there is a competition of antibody binding for the doxorubicin conjugate in the well and the analyte in solution. Following this incubation the wells of the plate were washed three times with 0.02 M TRIS, 0.9% NaCl, 0.5% Tween-80 and 0.001% Thimerosal, pH 7.8 to remove any material that was not bound. To detect the amount of doxorubicin antibody bound to the doxorubicin [5]-BSA conjugate in the wells, 100 μL of a goat anti-mouse antibody-HRP enzyme conjugate (Jackson Immunoresearch) diluted to a predetermined specific activity (approximately 1/2800) in PBS with 0.1% BSA, 0.05% ANS, 0.01% thimerosal, capable of binding specifically with murine immunoglobulins and producing a colored product when incubated with a substrate, were added to each well. After an incubation of 10 minutes at room temperature with shaking, during which the goat anti-mouse antibody—HRP enzyme conjugate binds to doxorubicin antibodies in the wells, the plates were again washed three times to remove unbound secondary conjugate. To develop a measurable color in the wells washing was followed by the addition of 100 μL of TMB (TMB Liquid Substrate), a substrate for HRP, to develop color in a 10 minute incubation with shaking at room temperature. Following the incubation for color development, 50 μL of stop solution (1.5% sodium fluoride in di $H_2O$) was added to each well to stop the color development and after 10 seconds of shaking the absorbance was determined at 650 nm with a 96-well plate reader. The amount of antibody in a well was proportional to the absorbance measured and inversely proportional to the amount of doxorubicin in the sample. The absorbance of the color in the wells containing analyte was compared to that with no analyte and a standard curve was generated. The $IC_{50}$ value for a given analyte was defined as the concentration of analyte that is required to inhibit 50% of the absorbance for the wells containing no analyte. The cross-reactivity of a given analyte was calculated as the ratio of the $IC_{50}$ for doxorubicin to the $IC_{50}$ for doxorubicin aglycone and expressed as a percent. When measured with an antibody as produced in Examples 7 and 8 with immunogen of Examples 3a, 3b, 4a & b the percent cross-reactivates relative to doxorubicin for doxorubicin aglycone was less than or equal to 10%. Results are in tables 1 & 2 below.

TABLE 1

Cross-Reactivity of Competitive Immunoassay using antibodies to doxorubicin [5]-BTG and KLH (Example 8) with plate coatings doxorubicin [5]-BSA conjugate (Examples 9b, 9c, 9d).

| Plate sensitized as in Example | Immunogen Example 4a % cross-reactivity | | Immunogen Example 4b % cross-reactivity | |
|---|---|---|---|---|
| | doxorubicin | doxorubicin-aglycone | doxorubicin | doxorubicin-aglycone |
| 9b | 100% | 5.7% | 100% | 8.6% |
| 9c | 100% | 10.0% | 100% | not measured |
| 9d | 100% | 8.8% | 100% | not measured |

TABLE 2

Cross-Reactivity of Competitive Immunoassay using a monoclonal antibody to doxorubicin [4]-BTG and -KLH (Example 7) with plate coating doxorubicin [5]-BSA conjugate (Examples 9b, 9c, 9d).

| Plate sensitized as in Example | Immunogen Example 3a % cross-reactivity | | Immunogen Example 3b % cross-reactivity | |
|---|---|---|---|---|
| | doxorubicin | doxorubicin-aglycone | doxorubicin | doxorubicin-aglycone |
| 9b | 100% | 10.6% | 100% | 1.5% |
| 9c | 100% | 12.9% | 100% | 3.9% |
| 9d | not tested | | 100% | 3.0% |

As seen from these tables, the antibodies of this invention are substantially selectively reactive with the active, parent form of doxorubicin and are not substantially cross-reactive with the inactive aglycone metabolite of doxorubicin.

What is claimed is:

1. An immunoassay for detecting doxorubicin in a sample comprising providing a mixture of a) said sample, b) an antibody selectively reactive with doxorubicin and not substantially cross-reactive with doxorubicin aglycone and c) a conjugate of a carrier having either a reactive thiol or amino group with a compound of the formula:

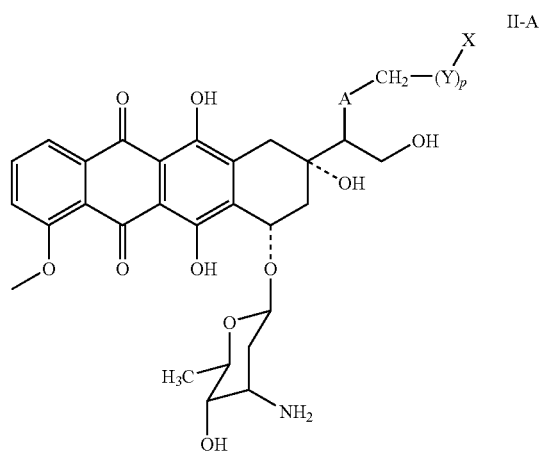

wherein A is

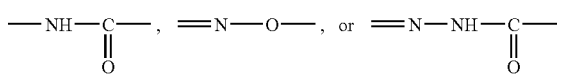

Y is an organic spacing group;

X is a functional group capable of binding to said carrier through said amino or thiol group; and p is an integer from 0 to 1;

or a compound of the formula:

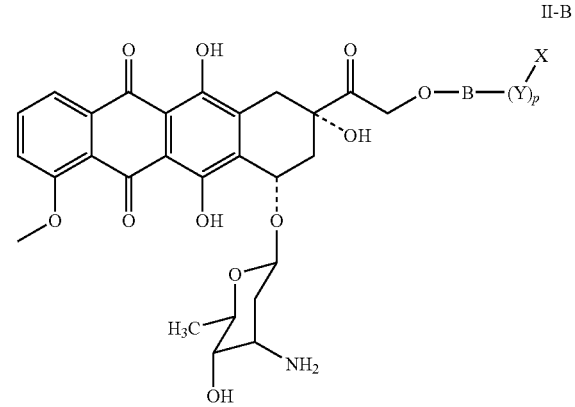

wherein X, Y and p are as above and B is —$CH_2$— or

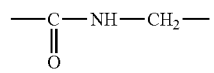

or mixtures comprising a conjugate of said carrier with a compound of Formula IIA and a conjugate of said carrier with a compound of Formula IIB;

causing the doxorubicin in the sample and said conjugate in said mixture to bind in said mixture with said antibody and thereafter measuring the amount of said conjugate in said mixture which is bound or unbound to said antibody whereby the presence of doxorubicin in the sample can be determined.

2. The process of claim 1, wherein the sample is a human sample.

3. The immunoassay of claim 2, wherein said antibody is generated from an immunogen comprising an immunogenic carrier having a reactive thiol or amino group conjugated to a compound of the formula:

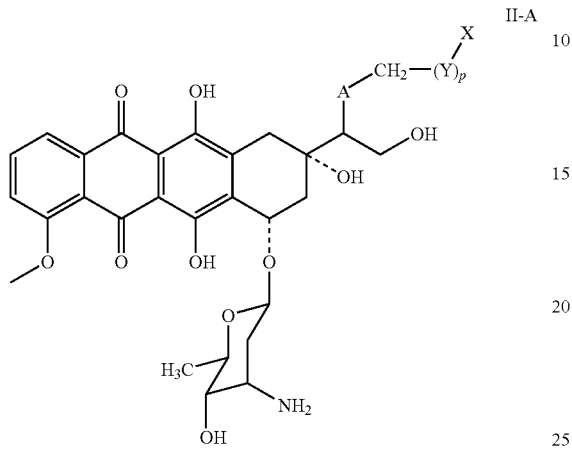

wherein p, X, Y and A are as above;
or a compound of the formula:

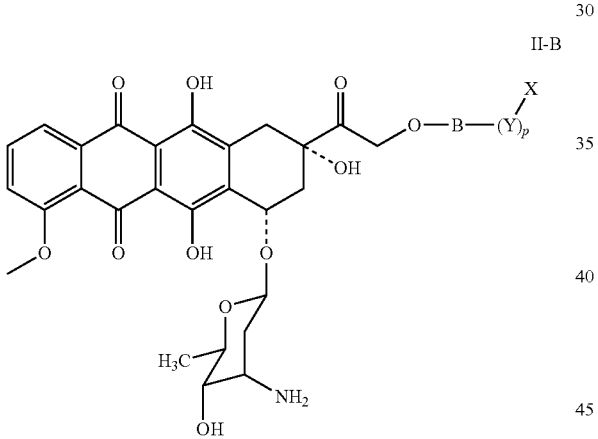

wherein p, Y, X and B are as above;
or mixtures thereof.

4. The immunoassay of claim 3, wherein the compound conjugated to said immunogenic carrier for generating the antibodies has the formula:

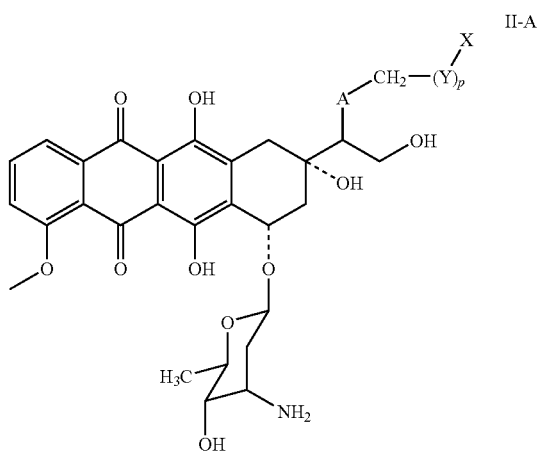

wherein p, X, Y and A are as above.

5. The immunoassay of claim 4, wherein the carrier contains a thiol group and X is the compound which is linked to the immunogenic polymer is a functional group capable of reacting with said thiol.

6. The immunoassay of claim 5, wherein X is

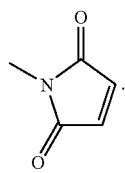

7. The immunoassay of claim 6, wherein Y is lower alkyl.

8. The immunoassay of claim 7 wherein the immunogenic carrier contains as the functional group

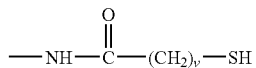

wherein v is an integer from 1 to 6.

9. The immunoassay of claim 2, wherein the antibody is attached to a solid support.

10. The immunoassay of claim 9, wherein the solid support is microtiter plates.

11. The immunoassay of claim 9, wherein the solid support is nanoparticles.

\* \* \* \* \*